United States Patent [19]

Tanaka et al.

[11] Patent Number: 4,714,767

[45] Date of Patent: * Dec. 22, 1987

[54] PROCESS FOR THE SEPARATION OF A BASIC AMINO ACID FROM A FERMENTATION BROTH USING CATION EXCHANGE RESINS

[75] Inventors: Kiyoshi Tanaka, Tokyo; Masaru Saeki, Saga; Tsutomu Matsuishi, Yanagawa; Yoshihiro Koga, Saga; Tetsuya Kawakita, Yokohama, all of Japan

[73] Assignee: Ajinomoto Co., Inc., Tokyo, Japan

[*] Notice: The portion of the term of this patent subsequent to May 5, 2004 has been disclaimed.

[21] Appl. No.: 753,881

[22] Filed: Jul. 11, 1985

[30] Foreign Application Priority Data

Jul. 11, 1984 [JP] Japan ............................ 59-143802

[51] Int. Cl.$^4$ ................. C07D 233/64; C07C 101/24
[52] U.S. Cl. ................................. 548/344; 210/259; 562/554
[58] Field of Search ..................... 548/344; 562/554

[56] References Cited

U.S. PATENT DOCUMENTS 4,663,048 5/1987 Tanaka et al. ................. 210/638

OTHER PUBLICATIONS

Chemical Abstracts, 104:184853a (1986)[JPN Kokai 60, 256, 392, Shiomi et al., 12/18/85].

Primary Examiner—Richard A. Schwartz
Attorney, Agent, or Firm—Oblon, Fisher, Spivak, McClelland, & Maier

[57] ABSTRACT

A process for separating basic amino acids from a liquid containing the same using cation exchange resin towers in series, which comprises effecting repetitive adsorption and elution steps in sequence, wherein the washing water employed in said adsorption and elution steps is obtained by recycling the latter portion of a liquid discharged from a first tower of the adsorption step into an adsorption step in a subsequent cycle, or by recycling a liquid discharged from a first tower at the elution step into an elution step in a subsequent cycle.

10 Claims, 7 Drawing Figures

PROCESS FOR THE SEPARATION OF A BASIC AMINO ACID FROM A FERMENTATION BROTH USING CATION EXCHANGE RESINS

BACKGROUND OF THE INVENTION

1. Field of the Invention

The present invention relates to a process for the separation of a basic amino acid from a fermentation broth using cation exchange resins.

2. Description of the Background

At present, basic amino acids are mainly produced by fermentation and, cation exchange resins are generally utilized for separating the basic amino acid from its fermentation broth. The use of the cation exchange resin generally entails an adsorption step in which a fermentation broth adjusted to a definte pH is brought into contact with a strongly acidic salt-type cation exchange resin such as ammonium-type one to adsorb a basic amino acid thereto and, an elution step in which the basic amino acid is eluted with an eluting agent such as ammonia water, and the cation exchange resin is regenerated into salt-type one. By repeating these two steps, the basic amino acid is separated from its fermentation broth.

One of the problems with the cation exchange resin step is that, at present, large quantities of water must be used. Namely, a fermentation broth and then washing water are fed into the resin tower in order to completely pass the fermentation broth through the cation exchange resin layer at the adsorption step. Similarly, at the elution step, washing water must be fed in order to completely pass the eluting agent. Further, suspended matters, etc. contained in the fermentation broth at the adsorption step accumulate in the cation exchange resin layer and, large quantities of washing water must be used to remove the accumulated solid. These not only increase the consumption amount of water but also increase the amount of liquid discharged. In addition, the concentration of the basic amino acid in the eluate is low and accordingly, much energy is required for condensing the eluate.

Various methods for reducing the amount of washing water to be used and energy required for condensation have been explored. Some of these methods have substituted various discharged liquids for the washing water such as, for example, the method described in Japanese Published Unexamined Patent Applications 12879/1975 and 11173/1977. However, these methods are quite complex and, therefore, increase production costs. Therefore, when using cation exchange resins in separating basic amino acids from solutions containing the same, it would be particularly desirable to be able to greatly reduce the amount of washing water used as well as to be able to greatly reduce the energy required for condensation of the eluate. However, to date, such a separation process has remained unknown.

Therefore, a need continues to exist for a process for the separation of a basic amino acid from a liquid containing the same using cation exchange resins which utilizes a reduced quantity of washing water and much less energy for the condensation of the eluate.

SUMMARY OF THE INVENTION

Accordingly, it is an object of the present invention to provide a process for separating basic amino acids from a liquid containing the same using cation exchange resins, which utilizes a greatly reduced quantity of washing water and much less energy for the condensation of the eluate.

It is also an object of this invention to provide a relatively simple process for separating basic amino acids from a liquid containing the same.

According to the present invention, the foregoing and other objects are attained by a process for separating basic amino acids from a liquid containing the same using a plurality of cation exchange resin towers in series, which comprises effecting repetitive adsorption and elution steps in sequence, wherein the washing water employed in said adsorption and elution steps is obtained by recycling the latter portion of a liquid discharged from a first tower at the adsorption step into an adsorption step in a subsequent cycle, or recycling a liquid discharged from a first tower at the elution step into an elution step in a subsequent cycle.

BRIEF DESCRIPTION OF THE DRAWINGS

Other objects, features and attendant advantages of the present invention will be more fully appreciated as the same becomes better understood from the following detailed description when considered in connection with the accompanying drawings and wherein.

DETAILED DESCRIPTION OF THE PREFERRED EMBODIMENTS

The present invention has been accomplished on the basis of the discovery that the amount of washing water to be used in conjunction with the adsorption and elution sequence with a cation exchange resin can be surprisingly reduced by recycling the latter portion of a discharged liquid from a first tower at the adsorption step into an adsorption step in a subsequent cycle or, by recycling a discharged liquid from a first tower at the elution step into an elution step in a subsequent cycle. Moreover, the energy required for condensation can be also surprisingly reduced by increasing the concentration of a basic amino acid in the eluate.

In particular, the present method effects a separation of basic amino acids from liquids containing the same using a plurality of cation exchange resin towers in series and repeating the adsorption and elution steps while moving the connections in sequence. The present method will now be explained in greater detail using, as an example, a three (3) tower adsorption-three (3) tower elution system. In such a system, the total number of cation exchange towers used is five (5) i.e., towers $R_1$, $R_2$, $R_3$, $R_4$ and $R_5$.

Starting Operation

Adsorption Step

Figure 1:
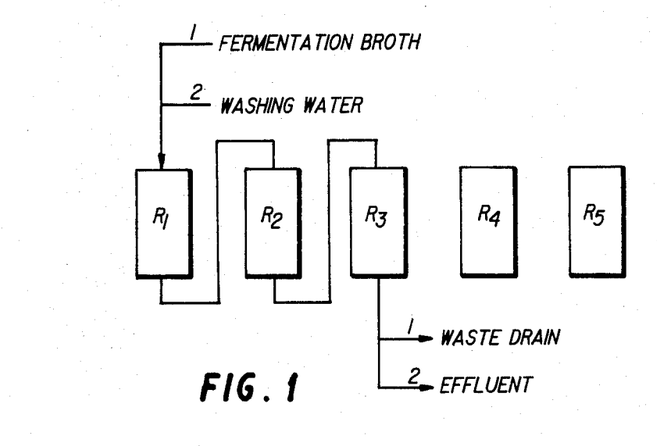
FIG. 1 illustrates the adsorption step in a three tower adsorption-three tower elution system, where each of tower $R_1$, $R_2$ and $R_3$ is connected in series and a fermentation broth is passed from tower $R_1$ followed by passing washing water therethrough, and then the waste drain and effluent are discharged.

Each tower of $R_1$, $R_2$ and $R_3$ is connected in series as shown below and, a fermentation broth is passed from $R_1$ tower followed by passing washing water. This is illustrated in FIG. 1.

From $R_3$ tower, a liquid (hereinafter referred to as "Waste drain") having a low concentration of impurities such as inorganic cations is first discharged and subsequently, a liquid (hereinafter referred to as "Effluent") having a high concentration of impurities is discharged.

Figure 2:
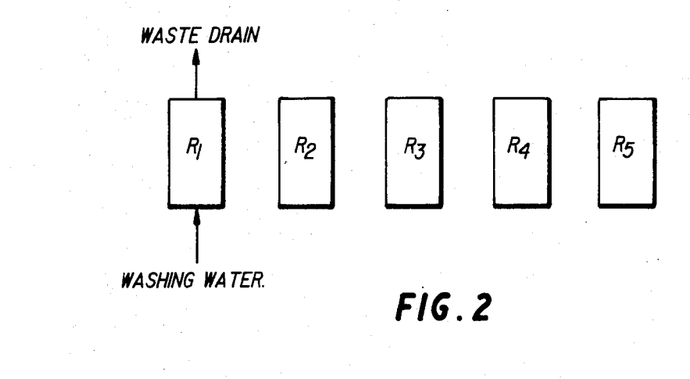
FIG. 2 illustrates the backwashing of tower $R_1$ with washing water.

Next, tower $R_1$ is subjected to back wash. This is illustrated in FIG. 2.

Figure 3:
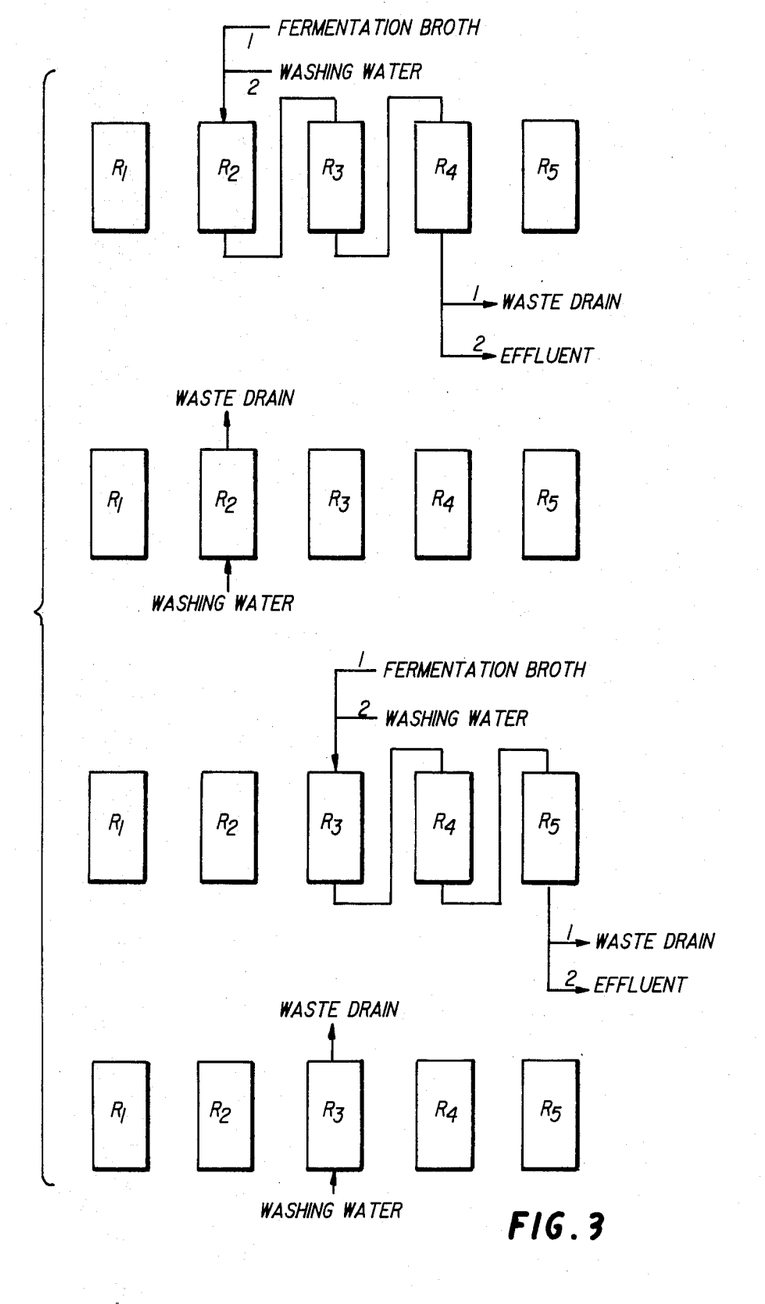
FIG. 3 illustrates moving one tower to another, and thereby repeating the previous adsorption and elution steps as one cycle.

While moving the towers one to another, the operation described above is repeated twice. This is illustrated in FIG. 3.

Elution Step

Figure 4:
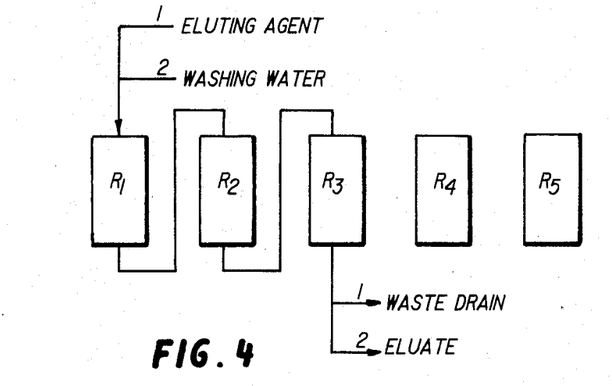
FIG. 4 illustrates the elution step in the same system, where each of tower $R_1$, $R_2$ and $R_3$ is connected in series, and an eluting agent is passed from tower $R_1$ followed by passing washing water therethrough, and then the waste drain and eluate are discharged.

Each tower of $R_1$, $R_2$ and $R_3$ is connected in series and, an eluting agent is passed from $R_1$ tower and then washing water is passed.

From $R_3$ tower a Waste drain is first discharged and subsequently, an eluate containing the basic amino acid is discharged. This is illustrated in FIG. 4.

Stationary Operation

Adsorption Step

Figure 5:
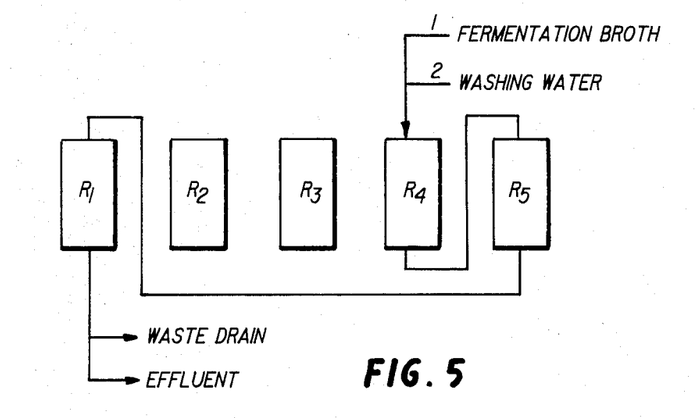
FIG. 5 illustrates the adsorption step in the same system, where each of tower $R_4$, $R_5$ and $R_1$ is connected in series and a fermentation broth, and subsequently washing water, is passed from tower $R_4$.

Each tower of $R_4$, $R_5$ and $R_1$ is connected in series and, a fermentation broth, and subsequently washing water, is passed from $R_4$ tower. This is illustrated in FIG. 5.

Figure 6:
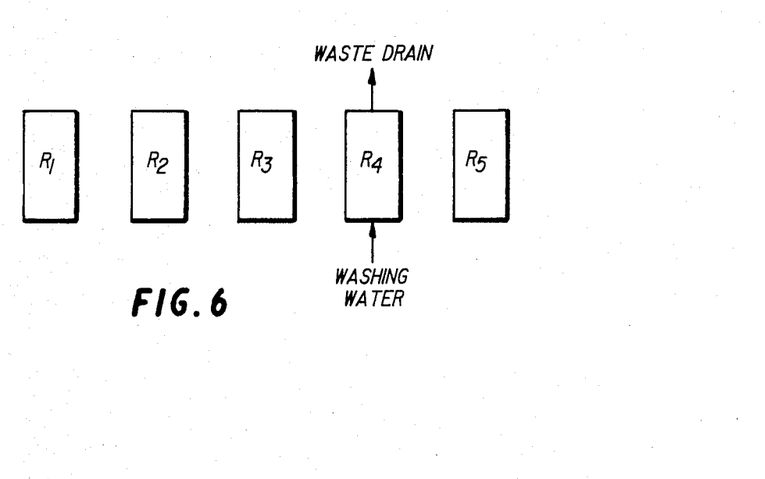
FIG. 6 illustrates the backwashing of tower $R_4$ with washing water.

Next, tower $R_4$ is subjected to backwashing. This is illustrated in FIG. 6.

Elution Step

Figure 7:
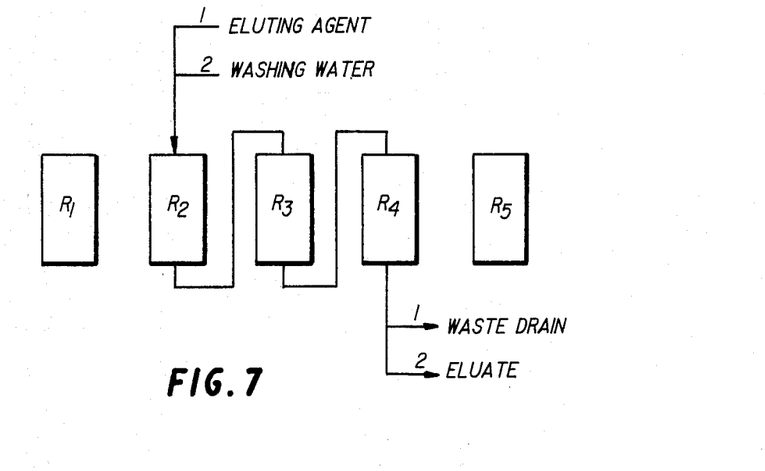
FIG. 7 illustrates the elution step in the same system, where each of tower $R_2$, $R_3$ and $R_4$ is connected in series, and an eluting agent, and then washing water, is passed from tower $R_2$.

Each tower of $R_2$, $R_3$ and $R_4$ is connected in series and, an eluting agent, and then washing water, is passed from $R_2$ tower. This is illustrated in FIG. 7 while moving one tower to another, these two steps, i.e., adsorption and elution, are repeated as one cycle.

The number of cation exchange resin towers connected at the adsorption step and the elution step may be appropriately varied. Depending upon the mode, the system is called a 2 tower adsorption-2 tower elution system, a 3 tower adsorption-3 tower elution system, a 4 tower adsorption-4 tower elution system, or the like.

The cation exchange resins to be used may be conventional resins, for example, DIAION SK-1B, Amberlite IR-120, and Duolite C-20 (all are trademarks), etc. and, depending upon the kind of eluting agents, cation exchange resins may be employed in the form of ammonium-type, sodium-type, etc.

The method of the present invention is particularly characterized by the fact that the latter portion of the discharged liquid from the first tower at the adsorption step or at the elution step is recycled to a step of the same kind.

In the aforesaid 3 tower adsorption-3 tower elution system, for example, the adsorption step is clearly explained. Each tower of $R_1$, $R_2$ and $R_3$ is connected and used. At the last part of the adsorption step, the first tower, $R_1$, is separated from $R_2$ tower, and discharged liquid from $R_1$ tower is collected (hereinafter, this liquid is referred to as the "After collected" liquid). Before passing fermentation broth through at the next cycle's adsorption step, the "after collected" liquid is passed through $R_4$ tower, which is the third tower at the adsorption step (hereinafter, this operation is referred to as "Pre-adsorption"). Such is similarly done also at the elution step. For example, each tower of $R_5$, $R_6$ and $R_1$ is connected and used. At the last part of the elution step, the first tower $R_5$ is separated from $R_6$ tower, and discharged liquid from $R_5$ tower is collected (hereinafter, referred to as "Recovered alkali"). "Recovered alkali" is used as a part of the next cycle's eluting agent.

It is appropriate that the "after collected" liquid starts to be collected at the adsorption step at a point of time when a rapid fall of the concentration of the basic amino acid in the discharged liquid from the first tower begins by the replacement and dilution with washing water. While this point of time varies depending upon the amount of water at the upper portion of the cation exchange resin layer, or the shape of cation exchange resin tower, etc., the optimum point of time generally occurs when passing washing water these through in an amount of approximately 0.4 to 0.7 RV. The "after collected" liquid contains large quantities of inorganic salts but small quantities of a basic amino acid. This liquid is used at the "Pre-adsorption" during the subsequent cycle's adsorption step. In this case, the liquid is adjusted to a pH of 1 to 2 to thereby associate the basic amino acid with divalent cations, by adding hydrochloric acid or sulfuric acid, for example, in order to improve the adsorptivity of the basic amino acid to the cation exchange resins, and the liquid is then passed through the third tower. In passing of the basic amino acid-containing solution after passing the pH-reduced liquid as such through the first tower, an increased ratio of divalent cations of the basic amino acids is produced and, in exchange therefor, the adsorptivity decreased. For this reason, the liquid is passed into the third tower which has a low adsorptivity for the basic amino acids.

It is appropriate that the liquid discharged at the elution step is switched at a point of time where the concentration of the eluting agent in the discharged liquid from the first tower begins to decrease by the replacement and dilution with washing water. If "Recovered alkali" is used as part of the eluting agent solution at a subsequent elution step, the concentration of the basic amino acid in the eluate can be further enhanced.

As a method for increasing the concentration of the eluate, the first portion of the eluate having a low concentration of the basic amino acid (hereinafter, this liquid is referred to as "Pre-eluate") may be eliminated in some instances. However, it is preferred that "Pre-eluate" be added to the "after collected" liquid to recover the basic amino acid from the combined liquids.

The basic amino acids which are to be purified by the method of the present invention include, for example, lysine, arginine, ornithine or histidine. Of course, any basic amino acid can be so purified. The solution to be fed to the cation exchange resin towers includes, in the case of a basic amino acid prepared by fermentation, a fermentation broth; a liquid obtained by separating bacteria therefrom; a solution of crude crystals; a mother liquor of crystalization, etc.; and in the case of a basic amino acid prepared by protein decomposition, basic amino acid fractions separated from protein hydrolysates, etc.

Conditions for cation exchange resin treatment may be conventional conditions. For example, the pH at the adsorption step may be adjusted to associate the basic amino acid with monovalent cations or divalent cations, depending upon the concentration of the basic amino acid and impurities present such as inorganic cations, etc. As eluting agents, ammonia, sodium hydroxide, or sodium chloride, for example, may be used.

In the method of the present invention, the amount of "Effluent" discharged from the final tower can be decreased and its treatment can be easily effected by recycling the "after collected" liquid from the first tower at the adsorption step into an adsorption step in a subsequent cycle. Further by recycling, the basic amino acids contained in the "after collected" liquid can be recovered and at the same time, the content of the resin layer can be adjusted to an appropriate pH value.

In addition, by recycling "Recovered alkali" from the first tower to an elution step of a subsequent cycle, the amount of the eluate can be decreased and at the same time, the concentration of the basic amino acid can be enhanced to thereby reduce the energy required for condensation.

According to the present invention, the amount of water to be used can be surprisingly reduced, and at the same time, the energy required for condensation can be surprisingly reduced, only by effecting modifications in the cation exchange resin operation, whereby the equipment required for treating waste liquid and effecting condensation procedures can be reduced and production costs can be decreased.

The present invention will now be further illustrated by certain examples and references which are provided for purposes of illustration only and are not intended to limit the present invention.

EXAMPLE

A solution having a L-lysine concentration of 9.3 g/dl, obtained by adding sulfuric acid to a lysine fermentation broth to adjust pH to 4.0, was used as a sample solution.

Using 5 towers ($R_1$, $R_2$, $R_3$, $R_4$ and $R_5$), in each of which 1 liter of strongly acidic cation exchange resin "Diaion Sk-1B" of $NH^+_4$-type was packed, the following resin operation was performed by a 3 tower adsorption-3 tower elution system.

Starting Operation

First, $R_1$ to $R_3$ towers were connected. From the upper portion of $R_1$ tower, 2.9 liters of the sample solution were passed at a rate of 30 ml/min. Then, 1 liter of washing water was passed at the same rate. $R_1$ tower was separated and subjected to backwash with 2.5 liters of water to eliminate the accumulated solid of bacteria, etc. $R_2$ to $R_4$ tower were connected and, 1.4 liter of the sample solution and then 1.0 liter of washing water were passed at a rate of 30 ml/min. $R_2$ tower was separated and subjected to back wash with 2.5 liters of water. Subsequently, $R_3$ to $R_5$ towers were connected and, similar operation was conducted. The discharged liquid was collected in the amount of 2.0 liters first from the last $R_5$ tower. Then, $R_3$ tower was separated from $R_4$ tower and, 0.4 liter of "after collected" liquid was collected from $R_3$ tower.

$R_1$ to $R_3$ towers in which adsorption and backwash had been completed were connected and, 1.8 liter of 3.5N ammonium water and then 1.0 liter of washing water were passed at a rate of 16 ml/min. From $R_3$ tower, 2.2 liters of the discharged liquid were collected. Thereafter, $R_1$ tower was separated from $R_2$ tower and, 0.6 liter of "Recovered alkali" (containing ammonia) was collected from $R_1$ tower. Out of liquids collected from $R_3$ tower, 1.5 liter which showed a lysine content of less than 1 g/dl was discarded and, 0.1 liter (Preeluate) having a 1 to 10 g/dl content and 0.6 liter having a content more than 10 g/dl were taken out, respectively, as a liquid for "Pre-adsorption" and for obtaining lysine.

Stationary Operation

A mixture of 0.4 liter of "after collected" liquid and 0.1 liter of "Pre-eluate" was adjusted to a pH of 1.5 by adding 0.01 liter of sulfuric acid thereto, which was passed through $R_1$ tower.

Next, $R_4$, $R_5$ and $R_1$ were connected. From $R_4$ tower, 1.4 liter of the sample solution, and then 1.0 liter of washing water, was passed at a rate of 30 ml/min. The discharged liquid was collected by 2.0 liters first from the last $R_1$ tower. Then, $R_4$ tower was separated from $R_5$ tower and, 0.4 liter of "after collected" liquid was collected from $R_4$ tower. Out of liquids collected from $R_1$ tower, first 0.5 liter was "Waste drain", next 1.5 liter was "Effluent". $R_4$ tower was subjected to back wash using 2.2 liters of washing water.

$R_2$ to $R_4$ towers were connected and, an eluting agent solution, prepared by mixing 0.074 liter of 25% ammonium water, 0.6 liter of "Recovered alkali" recovered at the preceding cycle and 0.126 liter of water, was passed at a rate of 16 ml/min and subsequently, 1.0 liter of washing water was passed at the same rate. The discharged liquid was collected by 1.2 liter first from $R_4$ tower and then, $R_2$ tower was separated from $R_3$ tower. From $R_2$ tower, 0.6 liter of "Recovered alkali" was collected. Out of 1.2 liter discharged from $R_4$ tower, 0.5 liter corresponding to the portion having a lysine content of less than 1 g/dl was discarded and, 0.15 liter of "Pre-eluate" and 0.55 liter of liquid for obtaining lysine were taken out.

The foregoing was effected in 1 cycle and, while moving the resin tower from one to another, the operation was repeated by 10 cycles.

On the other hand, for the purpose of comparison, 10 cycles in a stationary state were performed according to a conventional method. As resin towers, the same 5 towers as described above were separately provided and used.

The same operation method was used as in the aforesaid example except that either the "after collected" liquid at the adsorption step or "Recovered alkali" at the elution step were not performed, a mixture of 0.074 liter of 25% ammonium water and 0.726 liter of water was used as an eluting agent solution, and as the eluate, 1.4 liter of the portion having a lysine content of more than 1 g/dl was taken out for obtaining lysine but "Pre-eluate" was not taken out.

The results obtained are shown in the table below.

| | Method of Present Invention | Conventional Method |
|---|---|---|
| Necessary Amount of Eluting Agent (calculated as 25% ammonium water) l/cycle | 0.074 | 0.074 |
| Lysine concentration of the liquid for obtaining lysine g/dl | 20 | 8.8 |
| Amount of Effluent l/cycle | 1.5 | 1.9 |

Having now fully described this invention, it will be apparent to one of ordinary skill in the art that many changes and modifications can be made thereto without departing from the spirit or scope of the invention as set forth herein.

What is claimed is:

1. A process for separating basic amino acids from a liquid containing the same using a plurality of cation exchange resin towers in series, which comprises effecting repetitive adsorption and elution steps in sequence, wherein the washing water employed in said adsorption and elution steps is obtained by recycling the latter portion of a liquid discharged from a first tower of the adsorption step into an adsorption step in a subsequent cycle, or by recycling a liquid discharge from a first tower at the elution step into an elution step in a subsequent cycle.

2. The process according to claim 1, wherein said repetitive adsorption and elution steps are effected using a two (2) tower adsorption—two (2) tower elution system, a three (3) tower adsorption—three (3) tower elution system or a four (4) tower adsorption four (4) tower elution system.

3. The process according to claim 2, wherein said repetitive adsorption and elution steps are effected using a starting and a stationary operation with a three (3) tower adsorption—three (3) tower elution system, said towers being $R_1$, $R_2$ and $R_3$.

4. The process according to claim 3, wherein the adsorption step of the starting operation comprises:
   (a) connecting each of towers $R_1$, $R_2$ and $R_3$ in series and passing a liquid containing one or more basic amino acids from $R_1$ tower, followed by passing washing water therethrough; then
   (b) discharging a waste drain liquid having a low concentration of impurities therein first from tower $R_3$, and subsequently discharging an effluent liquid having a higher concentration of impurities; then
   (c) subjecting $R_1$ tower to backwashing; and
   (d) repeating the above cycle twice, while moving from one tower to another in sequence.

5. The process according to claim 3, wherein the elution step of the starting operation comprises:
   (a) connecting each of towers $R_1$, $R_2$ and $R_3$ in series and passing an eluting agent from $R_1$ tower, followed by passing washing water therethrough; then
   (b) discharging a waste drain liquid from tower $R_3$ and subsequently discharging an eluate containing said basic amino acid or acids.

6. The process according to claim 3, wherein the stationary operation comprises:
   (a) an adsorption step which comprises:
      (1) connecting each of towers $R_4$, $R_5$ and $R_1$ in series, and passing a liquid containing said basic amino acid or acids, and subsequently washing water from tower $R_4$; and
      (2) subjecting tower $R_4$ to backwashing; and
   (b) an elution step which comprises:
      (1) connecting each of towers $R_2$, $R_3$ and $R_4$ in series, and passing an eluting agent and, subsequently, washing water from tower $R_2$; and
   (c) repeating said adsorption and elution steps while moving sequentially from one tower to the next.

7. The process according to claim 1, wherein said cation exchange resins are ammonium-type or sodium-type resins.

8. The process according to claim 1, wherein said basic amino acid is lysine, arginine, ornithine or histidine or a mixture thereof.

9. The process according to claim 1, wherein said liquid containing said basic amino acid or acids is a fermentation broth, a liquid obtained by removing bacteria from a fermentation broth, a solution of crude crystals of said basic amino acid or acids, a mother liquor of crystallization of the same or a liquid containing basic amino acids obtained from protein hydrolyzates.

10. The process according to claim 1, wherein said eluting agent is solutions of ammonia, sodium hydroxide or sodium chloride.

* * * * *

UNITED STATES PATENT AND TRADEMARK OFFICE
CERTIFICATE OF CORRECTION

PATENT NO. : 4,714,767  
DATED : December 22, 1987  
INVENTOR(S) : Kiyoshi Tanaka et al Page 1 of 4

It is certified that error appears in the above-identified patent and that said Letters Patent is hereby corrected as shown below:

| Col. | Line | |
|---|---|---|
| 1 | 13, | delete "fermentation and," and insert --fermentation, and--, |
|  | 17, | delete "definte" and insert --definite--, |
|  | 20, | delete "thereto and," and insert --thereto, and--, |
|  | 36, | delete "layer and," and insert --layer, and--, |
| 2 | 61, | delete "cycle or," and insert --cycle, or--, |
| 3 | 13, | delete "below and," and insert --below, and--, |
|  | 29 & 30, | delete "series and," and insert --series, and--, |
|  | 32 | delete "discharged and" and insert --discharged, and,--, |
|  | 39 & 40, | delete "series and," and insert --series, and--, |
|  | 40, | delete "and subsequently" and insert --and, subsequently,--, |
|  | 47 & 48, | delete "series and," and insert --series, and--, |
|  | 49, | delete "FIG. 7 while" and insert --FIG. 7. While--, |
|  | 60 & 61, | delete "etc. and," and insert --etc., and--, |
| 4 | 28, | delete "these through" and insert --through these--, |

UNITED STATES PATENT AND TRADEMARK OFFICE
CERTIFICATE OF CORRECTION

PATENT NO. : 4,714,767
DATED : December 22, 1987
INVENTOR(S) : Kiyoshi Tanaka et al It is certified that error appears in the above-identified patent and that said Letters Patent is hereby corrected as shown below:

| Col. | Line | |
|---|---|---|
| 5 | 61, | delete "tower" and insert --towers--, |
| | | delete "connected and," and insert --connected, and--, |
| | | delete "liter" and insert --liters--, |
| | 65, | delete "connected and," and insert --connected, and--; |
| 6 | 1, | delete "tower and," and insert --tower, and--, |
| | 4, | delete "connected and," and insert --connected, and--, |
| | | delete "liter" and insert --liters--, |
| | 12, | delete "liter" and insert --liters--, |
| | 13, | delete "was discarded and," and insert --were discarded, and--, |
| | 13 & 14, | delete "(Preeluate)" and insert --"Pre-eluate"--, |
| | 25, | delete "1.4 liter" and insert --1.4 liters-- |
| | 29, | delete "tower and," and insert --tower, and--, |
| | 31, | delete "1.5 liter" and insert --1.5 liters--, |

UNITED STATES PATENT AND TRADEMARK OFFICE
CERTIFICATE OF CORRECTION

PATENT NO. : 4,714,767
DATED : December 22, 1987
INVENTOR(S) : Kiyoshi Tanaka et al It is certified that error appears in the above-identified patent and that said Letters Patent is hereby corrected as shown below:

Page 3 of 4

| Col. | Line | |
|---|---|---|
| 6 | 35, | delete "connected and," and insert --connected, and--, |
|  | 39, | delete "ml/min and" and insert --ml/min and,--, |
|  | 41, | delete "liter" and insert --liters--, |
|  | 42, | delete "and then," and insert --and, then,--, |
|  | 44, | delete "liter" and insert --liters--, |
|  | 47, | delete "discarded and," and insert --discarded, and--, |
|  | 50, | delete "cycle and," and insert --cycle, and,--, |
|  | 62, | delete "were" and insert --was--, |
|  | 65, | delete "liter" and insert --liters--, |
|  | 66, | delete "was taken" and insert --were taken--, |
| 7 | 32, | delete "discharge" and insert --discharged--, |
|  | 39, | delete "adsorption four" and insert --adsorption-four--, |
| 8 | 5 & 17, | delete "and subsequently" and insert --and, subsequently,--, |

UNITED STATES PATENT AND TRADEMARK OFFICE
CERTIFICATE OF CORRECTION

PATENT NO. : 4,714,767

DATED : December 22, 1987

INVENTOR(S) : Kiyoshi Tanaka et al

Page 4 of 4

It is certified that error appears in the above-identified patent and that said Letters Patent is hereby corrected as shown below:

| Col. | Line | |
|---|---|---|
| 8 | 24, | delete "and subsequently" and insert --and, subsequently,--, |
| NOTE: | | delete "back wash" and insert --backwash--, throughout |
| NOTE: | | delete "back washing" and insert --backwashing--, throughout |
| 4 | 7, | delete "After" and insert --after--, |

Signed and Sealed this

Twenty-sixth Day of July, 1988

*Attest:*

DONALD J. QUIGG

*Attesting Officer*     *Commissioner of Patents and Trademarks*